United States Patent [19]

Jennings et al.

[11] Patent Number: 5,843,461
[45] Date of Patent: Dec. 1, 1998

[54] GROUP B STREPTOCOCCUS TYPE II POLYSACCHARIDE-TETANUS TOXOID CONJUGATE VACCINES

[75] Inventors: Harold J. Jennings, Gloucester, Canada; Dennis L. Kasper, Newton Centre, Mass.

[73] Assignees: Brigham and Women's Hospital, Inc., Boston, Mass.; National Research Council of Canada, Ottawa, Canada

[21] Appl. No.: 924,401

[22] Filed: Aug. 22, 1997

Related U.S. Application Data

[63] Continuation of Ser. No. 142,886, Oct. 25, 1993, abandoned, which is a continuation of Ser. No. 949,970, Sep. 24, 1992, abandoned.

[51] Int. Cl.$^6$ ..................................................... A61K 39/09
[52] U.S. Cl. .................................... 424/244.1; 424/193.1; 424/198.1; 424/203.1; 530/403; 530/813; 530/825
[58] Field of Search .............................. 424/193.1, 198.1, 424/203.1, 244.1; 530/403, 813, 825

[56] References Cited

U.S. PATENT DOCUMENTS

| | | |
|---|---|---|
| 4,207,414 | 6/1980 | Kasper . |
| 4,284,537 | 8/1981 | Beachley . |
| 4,324,887 | 4/1982 | Kasper . |
| 4,356,170 | 10/1982 | Jennings . |
| 4,356,263 | 10/1982 | Kasper . |
| 4,367,221 | 1/1983 | Kasper . |
| 4,367,222 | 1/1983 | Kasper . |
| 4,425,330 | 1/1984 | Norcross et al. ........................ 424/92 |
| 4,619,828 | 10/1986 | Gordon .................................. 424/92 |
| 4,757,134 | 7/1988 | Blake et al. . |
| 4,789,735 | 12/1988 | Frank et al. . |
| 4,902,506 | 2/1990 | Anderson et al. ...................... 424/92 |
| 5,302,386 | 4/1994 | Kasper . |
| 5,367,223 | 11/1994 | Kasper . |

FOREIGN PATENT DOCUMENTS

| | | |
|---|---|---|
| 0 175 261 | 3/1986 | European Pat. Off. . |
| 0 206 852 | 12/1986 | European Pat. Off. . |
| 0 245 045 | 11/1987 | European Pat. Off. . |
| WO 87/06267 | 10/1987 | WIPO . |
| WO 89/00583 | 1/1989 | WIPO . |
| 9104049 | 4/1991 | WIPO . |

OTHER PUBLICATIONS

Attachment A (Work Statement) from Request for Proposal No. NIH–NIAID–DMID–92–13, issued by the Department of Health and Human Services for the National Institutes of Health on Jan. 21, 1992, entitled, "Prevention of Group B Streptococcal Infections in Neonatal and Infant Populations".

Abstract of Grant No. 2R37A23339–08, "Immunochemistry of Group B streptococcus polysaccharides (human, mice, rabbits)", Kasper, D.L., Principal Investigator, Fed. Research in Progress, printout of Jan. 26, 1993 for fiscal year 1992.

Abstract of Grant No. 5R01AI30628–02, "Prevention of perinatal group B streptococcal infections (human, mice, rabbits)", Kasper D.L., Principal Investigator, Fed. Research in Progress, printout of Jan. 26, 1993 for fiscal year 1992.

Baker, C.J., "Immunization to Prevent Group B Streptococcal Disease: Victories and Vexations", *Journal of Infectious Disease*, vol. 161, No. 5, pp. 917–921, May 1990.

Bittle, J.L., et al. "Vaccines Produced by Conventional Means to Control Major Infectious Diseases of Man and Animals", *Adv. Vet. Sci. Comp. Med.*, vol. 33, pp. 1–63, Feb. 1989.

Coleman, R.T., et al., "Prevention of Neonatal Group B Streptococcal Infections: Advances in Maternal Vaccine Development", *Obst. Gynec.*, vol. 80, No. 2, pp. 301–309, Aug. 1992.

Dintzis, "Rational Design of Conjugate Vaccines", *Pediatric Research*, vol. 32, No. 4, pp. 376–385, Oct. 1992.

Feldman, et al. "The immune response to the group B streptococcus", *Reviews in Medical Microbiology*, vol. 3, No. 1, Jan. 1992, pp. 52–58.

Givner, et al. "Pooled Human IgH hyperimmune for type III Group B Streptococci: Evaluation against multiple strains in vitro and in experimental diseases", *J. Infectious Diseases*, vol. 163, pp. 1141–1145, May 1991.

Insel, R.A., "Maternal Immunization of Prevent Neonatal Infections", *New England Journal of Medicine*, vol. 319, No. 18, pp. 1219–1220, Nov. 1988.

Lerner, R.A., et al. "The Development of Synthetic Vaccines", *The Biology of Immunologic Disease*, Dixon, F.J., et al., eds., Sinauer Associates: Sunderland, MA, pp. 331–338, 1983.

Madoff, et al., "Maternal Immunization of Mice with Group B Streptococcal Type III polysaccharide–beta C protein conjugate elicits protective antibody to multiple stereotypes", *J. Clin. Invest.*, vol. 94, pp. 286–292, Jul. 1994.

Madoff, L.C., et al., "Protection of Neonatal Mice from Group B Streptococcal Infection by Maternal Immunization with Beta C Protein", *Infect. Immun.*, vol. 60, No. 12, pp. 4989–4994, Dec. 1992.

Paoletti, L.C., et al. "Group B Streptococcus Type III Glycoconjugate Vaccines", *Trends in Glycosci. Glycotech.*, vol. 4, No. 17, pp. 269–278, May 1992.

Paoletti, et al. "Immunogenicity of Group B Streptococcus Type III Polysaccharide–tetanus Vaccine in Baboons", *Infection and Immunity*, vol. 64, No. 2, pp. 677–679, Feb. 1996.

(List continued on next page.)

*Primary Examiner*—James C. Housel
*Assistant Examiner*—Jennifer Shaver
*Attorney, Agent, or Firm*—Morgan & Finnegan, LLP

[57] ABSTRACT

This invention relates to antigenic conjugate molecules comprising the capsular polysaccharide of Group B streptococcus type II which are covalently linked to protein. This invention also relates to vaccines and methods of immunizing mammals, including humans against infection by Group B streptococcus type II (GBS II). Multivalent vaccines comprising the conjugate molecules of this invention and antigens to other pathogenic bacteria are also claimed.

33 Claims, 2 Drawing Sheets

OTHER PUBLICATIONS

Wilkinson, H.W., et al. "Type–Specific Antigens of Group B Type Ic Streptococci", *Infect. Immun.,* vol. 4, No. 5, pp. 596–604, Nov. 1971.

Ward et al, *"Haemophilus influenzae* Vaccines" in *Vaccines* Plotkin et al eds, W.B. Saunders Co. Philadelphia pp. 300–332, 1988.

Baker et al, Rev. Infec. Dis. 7(4):458–467, 1985.

Baker et al, New Eng. J. Med. 319(18): 1180–1185, 1988.

Boyer et al, Clin Res., 34(4) 962 A, 1986.

Wessels et al, Infect. Immun, 57(4):1089–1094, 1989.

Kasper et al, J. Clin Invest, 72:260–269, 1983.

Jenning et al, J. Biol. Chem. 258(3): 1793–1798, 1983.

Jennings et al, Biochemistry, 20(16): 4511–4518, 1981.

Sarvamangular et al, Proc. Natl Acad Sci, 88:7175–7179, 1991.

Heimas et al, The Opsomic Antibody Response of Female Rats to Type III Group B Streptococcal.

Immunization: a model for maternal Immunity, Vet. Immunol. Immunopath. 24:79–89, 1990.

Reuter et al, A Detailed Study of the Periodate Oxidation of Sialic Acids in Glycoproteins, Glycoconjugate J 6:35–44, 1989.

Facklam et al, "Streptococci and Aerococci" in Manual of Clinical Immunology, 4 ed. Lennette et al eds, American Society for Microbiology, 1985, pp. 154–175.

Wesseles et al, Immunogenicity in Animals of a Polysaccharide–Protein Conjugate Vaccine against Type III Group B Streptococcus; J. Clin. Invest 86:1428–1433, 1990.

Harold J. Jennings and C. Lugowski, "Immunochemistry of Groups A, B and C Meningococcal Polysaccharide Tetanus Toxoid Conjugates", *The Journal of Immunology,* 127:1011–1017 (1981).

Dick and Beurret (1989) "Glyconjugates of Bacterial Carobhydrafe Antigens—A Survey and Consideration of Designa dn Preparation Facts" Conjugate Vaccines) *In Contrib. Microbiol. Immunol* (Cruse, JM and Lewis, RE Tr. (eds.) Basel Karger vol. 10:48:114.

Jennings, (1983) "Capsular Polysaccharrides as Human Vaccines" *In Advances Carobhydrate Chemistry and Biochemistry,* vol. 41:155–207, Academic Press Inc. NY NY.

Paoletti (1992) Effects of Chain Length on the Immunogenicity in Rabbits of Group B Streptococcus Type III Oligosaccharride—Tetanus Toxoid Conjugate. *J. Clin. Invest.* 89:203–209.

Wessels, et al. (1989) "Isolation and Characterization of Type IV Group B Streptococcus Capsular Polysaccharide" *Infection and Immunity,* vol. 57, No. 4:1089–1094.

Kasper, et al. (1983) "Immunochemical Analysis and Immunogenicity of the Type II Group B Streptococcal Capsular Polysaccharide." *J. Clin Invest,* vol. 72:260–269.

Jennings, et al. (1982) "Structural Determination of the Capsular Polysaccharide Antigen of Type II Group B Streptococcus". *The Journal of Biological Chemistry,* vol. 258:1793–1798.

Paoletti, et al. (1990) An Oligosaccharide–Tetanus Toxoid Conjugate Vaccine against Type II Group B Streptococcus. *The Journal of Biological Chemistry,* vol. 265:18278–18283.

Rodewald, et al. (1992) "Neonatal Mouse Model of Group B Streptococcal Infection", *The Journal of Infectious Diseases,* vol. 166:635–9.

Paoletti (1992) "Group B Stretoccus Type II Polysaccharride—Tetanus Toxoid conjugate Vaccine" *Infection and Immunity,* vol. 60:4009–4014.

GROUP B STREPTOCOCCUS TYPE II POLYSACCHARIDE-TETANUS TOXOID CONJUGATE VACCINES

This is a continuation of application Ser. No. 08/142,886, filed on Oct. 25, 1993, now abandoned which is a continuation U.S. Ser. No. 07/949,970 filed Sep. 24, 1992, now abandoned.

This invention was made with Government support under NIH grant AI23339, AI30628 and AI28040 awarded by the National Institutes of Health. The Government has certain rights in this invention.

FIELD OF THE INVENTION

This invention relates to antigenic conjugate molecules comprising the capsular polysaccharide of Group B streptococcus type II which are covalently linked to protein. This invention also relates to vaccines and methods of immunizing mammals, including humans against infection by Group B streptococcus type II (GBS II). Multivalent vaccines comprising the conjugate molecules of this invention and antigens to other pathogenic bacterial are also claimed.

BACKGROUND OF THE INVENTION

Infections due to group B streptococci (GBS) are the most common single cause of sepsis and meningitis in newborns in developed countries (3, 31). Recent reports from some centers in the United States reflect a lower mortality (9 to 13%) than in series from the 1970s, perhaps as a result of earlier diagnosis and intensive care (1, 10). Nonetheless, fatal infections still occur, and equally important, up to 50% of survivors of GBS meningitis have chronic neurologic injury ranging from deafness and mild learning disabilities to profound motor, sensory, and cognitive impairment (3). Prevention rather than improved diagnosis or therapy is likely to have the most significant impact in further reducing GBS-related morbidity and mortality.

Because GBS capsular polysaccharide-specific antibodies appear to protect both experimental animals (23, 24) and human infants (4, 5) from GBS infection, some of the polysaccharides have been purified and tested in healthy adults as experimental vaccines (6). Were a safe and efficacious GBS vaccine available, it could be administered to women before or during pregnancy to elicit antibodies that would transfer to the fetus in utero and provide protection against neonatal infection. Of the three GBS polysaccharides (types Ia, II, and III) tested in volunteers, type II had the highest rate of immunogenicity, eliciting a type II-specific antibody response in 88% of previously nonimmune recipients (6). In neonates, the level of specific antibody required for protection against type II GBS infection is not precisely defined but has been estimated at 2 or 3 μg/ml (6). In a vaccine recipient who achieves an antibody response only slightly above the minimum required for protection, the amount of maternal antibody transferred across the placenta may be inadequate to protect a premature infant, because of the incomplete transfer to the fetus of material immunoglobulin G (IgG), or an infant with late-onset infection, since the half-life of maternal IgG antibodies in the newborn is about 25 days (13). Many of the infants in these two groups of patients might be protected if the magnitude of the specific antibody response to vaccination were higher. The transfer of maternal IgG to the fetus increases throughout the third trimester, so a higher maternal antibody level would provide protection earlier, i.e., to a more premature infant (16). Similarly, higher maternal levels would result in longer persistence of maternal antibodies in the infant, thereby providing protection against late-onset disease, as well.

The immunogenicity of several bacterial polysaccharide antigens has been increased by the attachment of suitable carrier proteins to polysaccharides or to derivative oligosaccharides (2, 14, 17–19, 22, 27, 29, 30, 34). Desirable properties of polysaccharide-protein conjugate vaccines include enhanced immunogenicity of the polysaccharide, augmented hapten-specific antibody response to booster doses, and a predominance of IgG class antibodies. Recently, we have been successful in developing a GBS III-Tetanus Toxoid (TT) vaccine by using the side chain sialic acid moieties as sites of directed protein coupling (33). The III-TT vaccine elicited GBS type III-specific, opsonically active antibodies, while the unconjugated type III polysaccharide was nonimmunogenic in rabbits (33).

SUMMARY OF THE INVENTION

This invention claims antigenic conjugate molecules comprising the capsular polysaccharide derived from Group B streptococcus type II and a protein component wherein two or more side chains terminating in sialic acid residues of the polysaccharide component are each linked through a secondary amine bond to protein.

Also claimed is a method of preparing a conjugate molecule of a capsular polysaccharide of Group B streptococcus type II and a protein comprising:

(a) subjecting the Group B streptococcus type II capsular polysaccharide to periodate oxidation sufficient to introduce an aldehyde group into one or more terminal sialic acid residues linked to the backbone of the polysaccharide;

(b) coupling the oxidized Group B streptococcus type II capsular polysaccharide to a protein through reductive amination to generate a secondary amine bond between the capsular polysaccharide and the protein.

Conjugate molecules prepared according to the method described above are also claimed.

This invention further claims a vaccine comprising the conjugate molecule described above. In addition, this invention claims multivalent vaccines comprising the conjugate molecule of the invention and at least one other immunogenic molecule capable of eliciting the production of antibodies to a pathogenic substance other than Group B streptococcus type II. In particular in addition to comprising the GBS type II conjugate molecules, the multivalent vaccine, according to the invention, further comprises other immunogenic molecules capable of eliciting the production of antibodies to pathogens selected from the group consisting of Group B streptococcus types Ia, Ib, III, IV and V, Haemophilus influenzae type b and *E. coli* type K1.

In another embodiment of this invention, a method of immunizing neonates is claimed wherein the vaccine comprising the conjugate molecules of the invention are administered in an immunogenic amount to a female human so as to produce antibodies capable of passing into a fetus conceived prior to or after administration of the vaccine in an amount sufficient to produce protection against infection in the neonate at birth.

A method of immunizing adults wherein a vaccine comprising the conjugate molecules of the invention are administered in an immunogenic amount to a human adult is also claimed. In addition, a method of immunizing adults wherein a vaccine comprising the conjugate molecules of the invention are administered in an immunogenic amount to a person at risk for being infected by Group B streptococcus type II is claimed.

Another embodiment of this invention is a method of immunizing dairy herds against bovine mastitis consisting of administering a vaccine comprising the conjugate molecules of the invention in an immunogenic amount to dairy cows.

DESCRIPTION OF THE PREFERRED EMBODIMENTS

Figure 1:
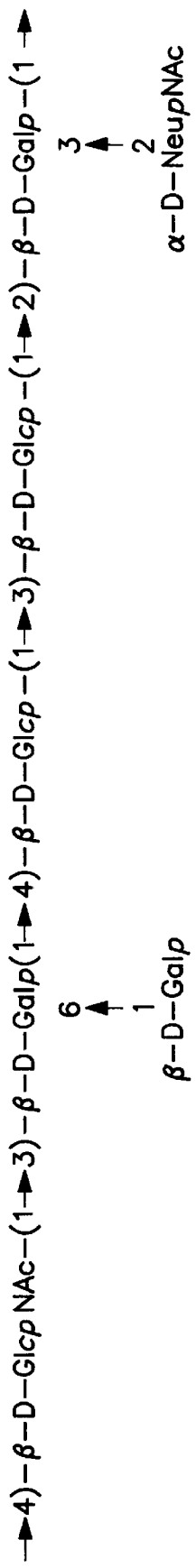
FIG. 1. Structure of the heptasaccharide repeating unit of type II GBS capsular polysaccharide 920).

Bacterial strains. GBS type II strain 18RS21 and type I$a$ strain 090 were originally obtained from the late Rebecca Lancefield of Rockefeller University and were maintained as frozen cultures at $-80°$ C. Strain 18RS21 was used in in vitro and in vivo assays and was the source of type II capsular polysaccharide used in the conjugate vaccine. Two GBS type II clinical isolates (strains S16 and S20) and type III strain M781 were obtained from the Channing Laboratory's culture collection.

Conjugation of GBS type II polysaccharide to TT. Type II capsular polysaccharide was purified from strain 18RS21 cells by methods described previously for purification of type III polysaccharide (33). The conjugation of type II polysaccharide to monomeric TT was performed by using techniques detailed previously for the conjugation of TT to GBS type III polysaccharide (33). In brief, native type II polysaccharide was size fractionated on a Sepharose CL-6B column (1.6 by 85 cm; Pharmacia Fine Chemicals). The material eluting at the center of the of the major peak was pooled, dialyzed against water, and lyophilized to yield material with a relative molecular weight of 200,000. Analysis of this material by $^1$H-nuclear magnetic resonance spectroscopy at 500 MHz confirmed the native type II polysaccharide structure (20) and the absence of group B antigen (26). The size-fractionated type II polysaccharide was subjected to mild oxidation with sodium meta-periodate (18). This procedure resulted in the conversion of a portion of the sialic acid residues on the polysaccharide to the eight-carbon analog of sialic acid, 5-acetamido-3,5-dideoxy-D-galactosylocrulosonic acid (33). The percentage of sialic acid residues oxidized was estimated by gas chromatography-mass spectrometry of the sialic acid residues and their oxidized derivatives as described previously (33).

The oxidized type II polysaccharide was linked to monomeric TT (Institute Armand Frappier, Montreal, Canada) by reductive amination as described previously (33). The TT was purified to its monomer from by gel filtration chromatography also as described previously (33). In brief, 10 mg of the periodate-treated type II polysaccharide and 10 mg of purified TT were dissolved in 0.6 ml of 0.1M sodium bicarbonate (pH 8.1). Sodium cyanoborohydride (20 mg) was added to the mixture and incubated at $37°$ C. for 5 days. The progress of the conjugation was monitored by fast protein liquid chromatography (FPLC) of small aliquots of the reaction mixture analyzed on a Superose 6 (Pharmacia) gel filtration column. The reaction was terminated when the height of the peak eluting at the void volume of the column (representing the high-molecular-weight conjugate) remained constant. The conjugate was purified by chromatography on a column of Biogel A, 0.5M (Bio-Rad Laboratories, Richmond, Calif.) as described previously (33). The protein content of the vaccine was estimated by the method of Lowry et al. (25), with bovine serum albumin as a standard. The carbohydrate content was assessed by the method of Dubois et al. (11), with purified type II polysaccharide as a standard. Examples of other proteins suitable for conjugating to the polysaccharide include diphtheria toxoid and the cross reactive material ("CRM") $CRM_{197}$.

Vaccination of rabbits with II-TT vaccine. Groups of three New Zealand White female rabbits (Millbrook Farms, Amherst, Mass.), each rabbit weighing approximately 3 kg, were vaccinated subcutaneously at four sites on the back with 50 μg of either uncoupled native type II polysaccharide or II-TT vaccine, each emulsified with complete Freund's adjuvant in a total volume of 2 ml. These animals received booster injections (50 μg) of vaccine prepared with incomplete Freund's adjuvant on days 20 and 41. Serum was obtained from each animal on days 0, 20, 34, 41, 55, and 70; filtered sterile; and stored at $-80°$ C.

ELISA. GBS type II-specific rabbit antibodies were quantified by enzyme-linked immunosorbent assay (ELISA) with goat anti-rabbit IgG conjugated to alkaline phosphatase (Tago Inc. Burlingham, Calif.) at 1/3,000 dilution. Microtiter plates (Immulon 2; Dynatech Laboratories, Inc., Chantility, Va.) were coated with 100 ng of purified type II polysaccharide linked to poly-L-lysine per well as described before (15, 33). Antibody titers were recorded as the reciprocal dilution that resulted in an $A_{405}$ of 20.3 when wells containing the reference serum (rabbit antiserum raised to whole BGS 18RS21 cells) at a dilution of 1/800 reached an $A_{405}$ of 0.5. The amount of antibody specific for the protein portion of the conjugate vaccine was estimated by ELISA by using plates coated with monomeric TT (100 ng per well). TT-specific IgG titers were recorded as the reciprocal dilution that resulted in an $A_{405}$ of $\geq .3$ 35 min after addition of the substrate, p-nitrophenyl phosphate (Sigma 104 phosphatase substrate tablets; Sigma Chemical Co.).

Separation of IgG and IgM from Immune rabbit serum. Protein A-agarose affinity column chromatography (Pierce Chemical Co., Rockford, Ill.) was used to separate immunoglobulins (IgG and IgM) from 0.5 ml of pooled immune rabbit serum, obtained on day 70, raised to II-TT vaccine as described elsewhere (28). Separation of antibody classes was confirmed with type II polysaccharide-coated ELISA plates with goat anti-rabbit IgG (γ and light chain specific; Tago) used at 1/500 dilution and goat anti-rabbit IgM (μ chain specific; Sera-Lab, Westbury, N.Y.) used at a 1/200 dilution.

Competitive ELISA. The specificity of rabbit serum raised to the II-TT vaccine was determined by competitive ELISA with homologous (type II) and heterologous (types I$a$ and III) polysaccharides as inhibitors. Epitope specificity of vaccine-induced pooled rabbit serum (obtained on day 70) was examined with native and desialylated type II polysaccharide and β-O-methylgalactopyranose as inhibitors of antibody binding. Native type II polysaccharide was desialylated by treatment with 6% acetic acid at 80° C. for 2 h. Polysaccharide inhibitors were serially diluted 4-fold and mixed with an equal volume (75 µl) of pooled rabbit serum (diluted 10,000-fold) obtained on day 70 after vaccination with II-TT vaccine. This mixture (100 µl) was then added to type II polysaccharide-coated ELISA wells. Alkaline phosphatase-conjugated anti-rabbit IgG was used as the secondary antibody at a dilution of 1/3,000. Results are expressed as follows: % inhibition–[$A_{405}$ with no inhibitor $-A_{405}$ with inhibitor]/$A_{405}$ with no inhibitor]×100.

In vitro antibody-mediated killing of GBS. The ability of vaccine-induced rabbit antibodies to opsonize GBS cells for subsequent killing by human peripheral blood leukocytes was assessed by an in vitro opsonophagocytosis assay (7,8).

Passive protection of mice by vaccine-induced rabbit antibodies. Groups of 10 Swiss-Webster outbred female mice (Taconic Farms, Germantown, N.Y.), each mouse weighing 18 to 20 g, were injected intraperitoneally with 0.2 ml of pooled serum (day 70) from rabbits vaccinated with either type II polysaccharide or II-TT vaccine. The titer, as measured by ELISA, of the pooled serum obtained on day 70 from rabbits immunized with type II polysaccharide was 100, and that of II-TT vaccine was 12,800. Control groups of five mice received pooled preimmunization rabbit serum or pooled antiserum raised to uncoupled TT (27). Twenty-four hours later, mice were challenged with type II strain 18RS21 ($1.5 \times 10^5$ CFU per mouse) in a total volume of 1.0 ml of Todd-Hewitt broth. The challenge dose for each strain was previously determined to be lethal for >90% of mice of similar weights and ages. Surviving mice were counted daily for three subsequent days.

Statistical Analysis. Fisher's exact test was used to compare the abilities of different rabbit sera to passively protect mice against lethal GBS infection.

RESULTS

Preparation and composition of II-TT vaccine. GBS II-TT vaccine was prepared by methods detailed previously for the construction of the GBS type III conjugate vaccine (33). Controlled periodate oxidation of type II GBS polysaccharide resulted in the modification of 7% of the polysaccharide's sialic acid residues as determined by gas chromatography-mass spectrometry analysis. Monomeric TT was covalently linked to modified sialic acid sites on the type II polysaccharide by reductive amination. The purified II-TT vaccine contained 32% (wt/wt) protein and 68% (wt/wt) carbohydrate. The final yield of II-TT vaccine was 7.8 mg, or 39%.

Immunogenicity of II-TT vaccine in rabbits. The immunogenicities of the II-TT vaccine and native type II polysaccharide were compared in rabbits. An increase in type II-specific antibody was seen following the primary dose of II-TT vaccine (Table 1). A booster dose of vaccine further increased the antibody response. Antibody levels remained unchanged or rose slightly following a second booster, dose on day 41 and were sustained throughout the remainder of the study (Table 1). In contrast to the II-TT vaccine, uncoupled native GBS type II polysaccharide failed to elicit a specific antibody response (Table 1). Animals vaccinated with the II-TT vaccine also developed antibodies to TT, achieving approximately a 3-$\log_{10}$ increase over preimmunization levels.

TABLE 1

GBS type II polysaccharide-specific antibody titers of rabbits vaccinated with native type II polysaccharide or II-TT vaccine

| Vaccine and rabbit | Antibody titer in ELISA as day:[a] | | | | | |
|---|---|---|---|---|---|---|
| | 0 | 20[b] | 34 | 41[b] | 55 | 70 |
| Native type II polysaccharide | | | | | | |
| 1 | 100 | 100 | 100 | 200 | 100 | 100 |
| 2 | 100 | 100 | 100 | 100 | 100 | 100 |
| 3 | 200 | 100 | 100 | 100 | 100 | 100 |
| II-TT | | | | | | |
| 1 | 100 | 400 | 3,200 | 3,200 | 6,400 | 12,800 |
| 2 | 100 | 1,600 | 3,200 | 6,400 | 6,400 | 25,600 |
| 3 | 100 | 6,400 | 12,800 | 25,600 | 12,800 | 12,800 |

[a]A value of 100 indicates an antibody titer of ≦100. Values are the means of duplicate determinations. Rabbits were vaccinated subcutaneously with 50 µg of vaccine emulsified with complete Freund's adjuvant on day 0.
[b]Booster doses with incomplete Freund's adjuvant were administered.

Figure 2:
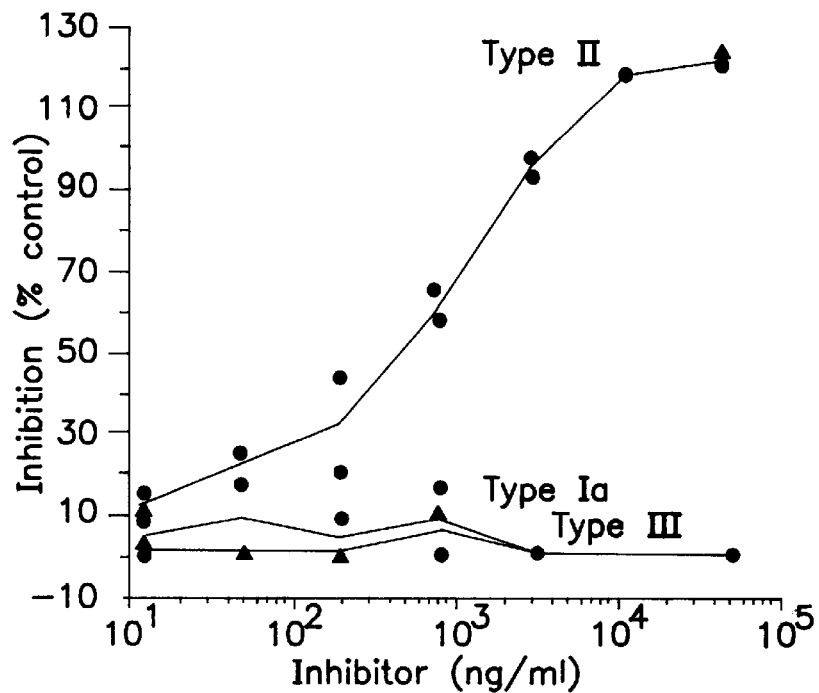
FIG. 2. GBS type II polysaccharide competitive ELISA. GBS type I$a$ (○), type II (●), and type III (▲) polysaccharides were used as inhibitors of II-TT vaccine antibody binding to plates coated with type II polysaccharide. Results are expressed as percentages of inhibition relative to that of control wells that lacked inhibitor.

Antigenic properties of vaccine-induced rabbit sera. The conjugation of polysaccharide to a protein carrier should not alter important antigenic epitopes found on the polysaccharide in its native form. We tested the specificity of II-TT vaccine-induced antibodies by competitive ELISA using homologous and heterologous GBS polysaccharides as inhibitors. Native type II polysaccharide at a concentration of 450 ng/ml inhibited 50% of the binding of rabbit antibodies raised to II-TT vaccine (FIG. 2). GBS type Ia and type III polysaccharides did not inhibit binding of serum raised to II-TT vaccine even at concentrations as high as 500 µg/ml. (FIG. 2). These result verify the serotype specificity of II-TT vaccine-induced antibodies for the target antigen and indicate preservation of antigenic epitopes of the polysaccharide portion of the conjugate vaccine.

Figure 3:
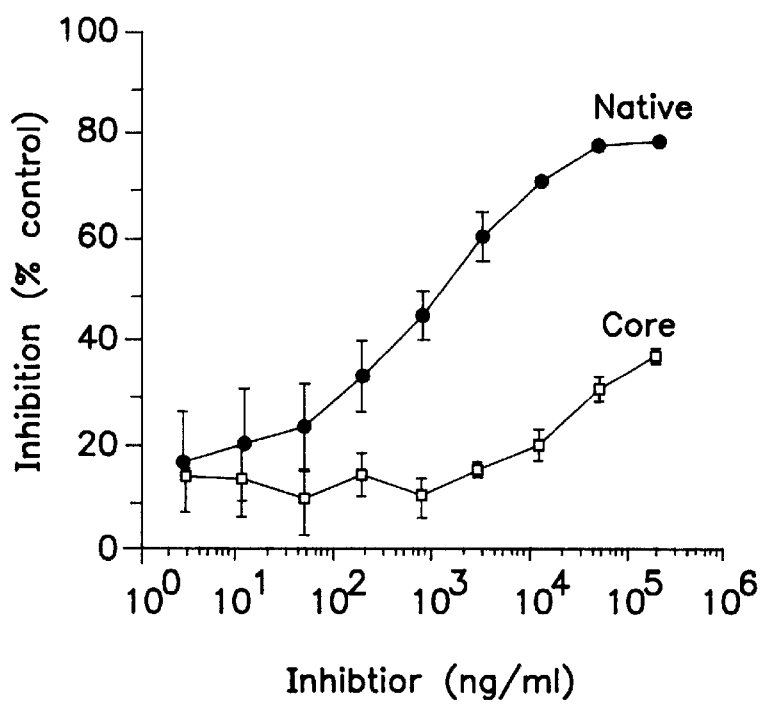
FIG. 3. GBS type II polysaccharide competitive ELISA. Native (●) and desialylated or core (□) type II polysaccharides were used as inhibitors of antibodies elicited by II-TT vaccine. Datum points are means (with standard deviations) of triplicate determinations. Results are expressed as percentage of inhibition relative to that of control wells that lacked inhibitor.

To determine whether the epitope influenced by sialic acid was maintained during the preparation of II-TT vaccine, native and desialylated type II polysaccharides were used in a competitive ELISA as inhibitors of binding of rabbit antibodies raised to II-TT vaccine. Desialylation of the polysaccharide was accomplished by treatment with 6% acetic acid at 80° C. for 2h. Quantitative removal of sialic acid residues was confirmed by the thiobarbituric acid assay (32) with N-acetylneuraminic acid (Sigma) as the standard. The $K_{av}$ of native type II polysaccharide before acid treatment was 0.49, whereas the $K_{av}$ of acid-treated polysaccharide was 0.52 on a Superose 6 FPLC column (LKB-Pharmacia, Sweden), indicating a slight reduction in molecular size of the polysaccharide due to the loss of the side chain sialic acid residues that make up 20% of the native polysaccharide by weight. Even 200 µg of desialylated GBS type II polysaccharide per ml inhibited by 33% of the binding of II-TT vaccine antibodies to native type II polysaccharide (FIG. 3). The relatively poor recognition of the desialylated or core type II polysaccharide by II-TT vaccine antiserum was confirmed by immunoelectrophoresis gels, which showed a precipitin band formed with the native but not the core type II polysaccharide (not shown). Binding of II-TT vaccine antisera to native type II polysaccharide could not be inhibited with β-O-methylgalactopyranose used at a concentration range of 0.01 to 10 mg/ml (not shown).

In vitro activity of GBS vaccine-induced antibodies. The ability of immune serum to opsonize GBS for killing by human peripheral blood leukocytes in vitro has correlated with protective efficacy against GBS in animal protection experiments (27,33). Antibodies raised in the three rabbits vaccinated with II-TT vaccine enhanced the killing of GBS type II strain 18RS21 by $\geq 1.8$ $\log_{10}$ (Table 2). Preimmunization rabbit serum or serum from rabbits vaccinated with native GBS type II polysaccharide or uncoupled TT failed to enhance the in vitro killing of GBS (Table 2). Vaccine-induced rabbit antibodies promoted the killing by human blood leukocytes of two GBS type II clinical isolates (strains S16 and S20) by $\geq 1.8$ $\log_{10}$ compared with preimmunization rabbit serum (Table 3). Rabbit serum to II-TT vaccine was determined to be serotype specific, as it failed to promote the in vitro killing of heterologous (types Ia and III) GBS strains (Table 3).

TABLE 2

In vitro opsonophagocytic killing of GBS type II strain 18RS21 by rabbit antiserum raised to native type II polysaccharide, II-TT vaccine, or TT

| Serum source | CFU | | GBS killed |
|---|---|---|---|
| (day of collection) | 0 min | 60 min | ($\log_{10}$) |
| Type II polysaccharide (70)[b] | $4.3 \times 10^6$ | $6.6 \times 10^6$ | −0.19 |
| II-TT vaccine (0) | $6.0 \times 10^6$ | $6.4 \times 10^6$ | −0.03 |
| II-TT vaccine (70) | | | |
| Rabbit 1 | $4.0 \times 10^6$ | $5.7 \times 10^4$ | 1.85 |
| Rabbit 2 | $4.3 \times 10^6$ | $2.7 \times 10^4$ | 2.20 |
| Rabbit 3 | $3.9 \times 10^6$ | $4.3 \times 10^4$ | 1.96 |
| TT (70) | $4.2 \times 10^6$ | $6.9 \times 10^6$ | −0.21 |
| None | $3.9 \times 10^6$ | $7.1 \times 10^6$ | −0.26 |

[a]Reaction mixture contained serum (at a final assay concentration of 1%) to be tested, type II GBS-absorbed human serum as a source of complement, human peripheral blood leukocytes, and type II GBS 18RS21. Values are means of duplicate determination.
[b]Rabbit serum collected following the primary dose of native type II polysaccharide in complete Freund's adjuvant.

TABLE 3

In vitro opsonophagocytic killing of GBS strains by preimmunization and immune rabbit serum raised to II-TT vaccine

| | GBS killed ($\log_{10}$)[a] | |
|---|---|---|
| GBS type and strain | Preimmunization (day 0) | Immune II-TT vaccine (day 70) |
| II | | |
| 18RS21 | −0.36 | 1.98 |
| S16 | 0.96 | 2.78 |
| S20 | −0.01 | 1.84 |
| I 090 | ND | −0.51 |
| III M781 | ND | −0.54 |

[a]CFU ($\log_{10}$) at 60 min - CFU ($\log_{10}$) at 0 min. Reaction mixture contained serum to be tested, type II GBS-absorbed human serum as a source of complement, human peripheral blood leukocytes, and type II GBS I8SR21. Values are means of duplicate determinations. ND, not done.

Protein A-affinity-purified IgG and IgM were obtained from pooled serum raised to II-TT vaccine (28). The specificity of each Ig fraction was confirmed by ELISA with class-specific secondary antibody. The $A_{405}$S of the IgM and IgG fractions (diluted 1/100) were 0.384 and 0.009, respectively, with $\mu$-chain-specific conjugate and 0.086 and 2.367, respectively, with goat anti-rabbit IgG ($\gamma$ and light chain specific). Isolated IgM and IgG were tested for their abilities to enhance opsonic killing of type II GBS by human blood leukocytes. Unfractionated sera raised to II-TT vaccine diluted 1:100 and an equivalent 1:100 dilution of the IgG fraction from the same sera promoted killing of type II GBS by $1.65 \pm 0.22$ and $0.95 \pm 0.09$ $\log_{10}$, respectively. In contrast, type II GBS were not killed but grew in the presence of preimmunization serum ($-0.39 \pm 0.13$ $\log_{10}$) and IgM-enriched fraction from serum raised to II-TT vaccine ($-0.28 \pm 0.09$ $\log^{10}$) in the opsonophagocytic assay.

Mouse protection assay. To test the in vivo protective abilities of vaccine-induced antibodies, mice were passively immunized with pooled II-TT vaccine sera (day 70) 24 h prior to challenge with type II GBS 18RS21. Previously, the challenge does was determined to be lethal for 90 to 100% of mice tested. Complete (100%) protection was afforded to groups of mice that received serum raised to GBS II-TT vaccine, whereas only one of five mice receiving prevaccination serum survived (Table 4). There were no survivors among mice that received serum from rabbits vaccinated with either uncoupled type II polysaccharide or uncoupled TT (Table 4).

TABLE 4

Passive protection of Swiss-Webster outbred mice against GBS type II strain 18RS21 with sera from rabbits vaccinated with native type II polysaccharide II-TT vaccine, or TT[a]

| Rabbit serum[b] (day of collection) | No. of survivors/ total no. of mice[c] | % Survival |
|---|---|---|
| II-TT vaccine (70) | 10/10 | 100[d] |
| II-TT vaccine (0) | 1/5 | 20 |
| Type II polysaccharide (70) | 0/10 | 0 |
| TT (70) | 0/5 | 0 |

[a]Mice were given a 90% lethal dose ($1.5 \times 10^5$ CFU per mouse) of GBS.
[b]Serum samples from three rabbits were pooled.
[c]Survival was determined 72 h after challenge.
[d]P = 0.0037 compared with preimmunization (day 0) values.

The coupling strategy used with GBS type III polysaccharide, first developed for meningococcal polysaccharide (18), may be applicable to all GBS capsular polysaccharide antigens, since they all contain sialic acid. However, unlike the other GBS polysaccharides that have sialic acid as the terminal saccharide of di- or trisaccharide side chains, the GBS type II polysaccharide has a repeating unit that bears sialic acid as the sole sugar on one of the two monosaccharide side chains (9, 20). In constructing the GBS type II conjugate vaccine, we oxidized 7% of sialic acid residues on the type II polysaccharide and used these as sites for coupling the polysaccharide to TT. Purified II-TT vaccine eluted in the void volume of a Superose 6 column (compatible with a molecular weight of >$10^6$) and was composed of 68% (wt/wt) carbohydrate and 32% (wt/wt) protein.

II-TT vaccine emulsified with adjuvant was immunogenic in rabbits in contrast to uncoupled native type II polysaccharide, which failed to elicit type II polysaccharide-specific antibody. Two of three rabbits immunized responded strongly 3 weeks after a single dose of II-TT vaccine. Optimal type-specific antibody was achieved in all three rabbits 3 weeks after a booster dose of II-TT vaccine. Further increases in type II-specific antibody titer were not seen after the third dose of II-TT vaccine. Results from in vitro and in vivo experiments indicated that antibodies raised to II-TT vaccine were functionally active against type II GBS. Serum from each of three rabbits vaccinated with II-TT vaccine promoted the in vitro killing of type II GBS by human peripheral leukocytes and provided outbred mice with complete (100%) protection against a lethal dose of type II GBS. II-TT vaccine antiserum was opsonically active against homologous GBS strains (18RS21, S16, and S20) but not heterologous GBS serotypes (types Ia and III) tested.

Whereas native type II polysaccharide inhibited binding of II-TT vaccine antisera to type II polysaccharide-coated ELISA wells, <40% inhibition was obtained with desialylated type II polysaccharide, even when it was used at a concentration of 200 µg/ml. This result suggests that an important antigenic determinant of type II polysaccharide is dependent on the presence of sialic acid residues. This result corroborated those obtained with rabbit antisera raised to whole type II organisms (21). However, ELISA inhibition experiments using β-O-methylgalactopyranose as an inhibitor indicated that rabbit antisera raised to II-TT vaccine did not contain galactose-specific antibodies. No inhibition of binding of II-TT vaccine antiserum to type II native polysaccharide was obtained even with β-O-methylgalactopyranose at a concentration of 10 mg/ml. Therefore, the side chain galactose does not appear to be an immunodominant epitope of type II polysaccharide when the polysaccharide is coupled to TT. These results are in contrast to immunochemical studies performed with rabbit sera raised to whole type II GBS organisms (12,21) in which the galactose side chain appeared to be one of two immunodominant sites, along with a sialic acid-dependent epitope, of type II polysaccharide. Whole type II GBS cells used in previous studies (12,21) and not cultured in pH-controlled conditions may possess polysaccharides that, to some degree, lack sialic acid. Under these circumstances, the side chain galactose might be major antigenic epitope. The source of type II polysaccharide used to synthesize the II-TT vaccine was a culture of type II GBS maintained at a pH of 7.0; a final analysis confirmed that sialic acid constituted ~20% (wt/wt) of the polysaccharide. We cannot exclude the possibility that coupling type II polysaccharide to TT altered the conformation of the polysaccharide, thereby rendering the galactose epitope unavailable for recognition by the host immune system. Although II-TT vaccine-induced rabbit antiserum lacked galactose-specific antibodies, it was fully functional in vitro and in vivo against type II GBS organisms. Neither chemical modification of some of the sialic acid residues nor the subsequent binding of TT to these sites altered critical antigenic epitopes necessary to elicit functional type II-specific antibody. That purified IgG from rabbit sera raised to II-TT vaccine promoted killing in vitro of type II GBS by human leukocytes suggests that not only was the immunogenicity of type II polysaccharide increased by conjugating it to TT but also that functional IgG antibodies were elicited.

Like III-TT vaccine, II-TT vaccine demonstrated improved immunogenicity in rabbits compared with active polysaccharide and elicited opsonically active IgG in rabbits despite difference in polysaccharide structure, position of the sialic acid on the polysaccharide to which TT was linked, and vaccine composition. We anticipate that GBS polysaccharide-protein conjugates of this design will ultimately constitute components of a multivalent GBS vaccine capable of providing protection against the GBS serotypes most often associated with disease in humans.

REFERENCES

1. Adams, W. G., J. Kinney, A. Schuchat, C. Collier, C. Papasian, H. Kilbride, F. Rledo, and C. Broome, 1991, Program Abstr. 31st Intersci, Conf. Antimicrob. Agents Chemother., abstr. 1056.
2. Avery, O. T., and W. F. Goebel, 1931. Chemo-immunological studies on conjugated carbohydrate-proteins. V. The immunological specificity of an antigen prepared by combining the capsular polysaccharide of type III pneumococcus with foreign protein. J. Exp. Med. 54:437–447.
3. Baker, C. J., and M. S. Edwards, 1990, Group B streptococcal infections, p. 742–811, In J. S. Remington and J. O. Klein (ad.), Infectious diseases of the fetus and newborn infant. The W. B. Saunders Co., Philadelphia.
4. Baker, C. J., M. S. Edwards, and D. L. Kasper, 1981, Role of antibody to native type III polysaccharide of group B Streptococcus in infant infection, Pediatrics 68:544–549.
5. Baker, C. J., and D. L. Kasper, 1976. Correlation of material antibody deficiency with susceptibility to neonatal group B streptococcal infection, N. Engl. J. Med. 294:753–756.
6. Baker, C. J., and D. L. Kasper, 1985. Group B streptococcal vaccines. Rev. Infect. Dis. 7:458–467.
7. Baker, C. J., M. A. Rench, M. S. Edwards, R. J. Carpenter, B. M. Hays, and D. L. Kasper, 1988. Immunization of pregnant women with a polysaccharide vaccine of group B Streptococcus. N. Engl. J. Med. 319:1180–1220.
8. Baltimore, R. S., D. L. Kasper, C. J. Baker, and D. K. Goroff, 1977. Antigenic specificity of opsonophagocytic antibodies in rabbit anti-sera to group B streptococci. J. Immunol. 118:673–678.
9. De Cueninck, B. J., T. F. Grebar, T. K. Eisenstein, R. M. Swenson, and G. D. Schockman, 1983. Isolation, chemical composition, and molecular size of extracellular type II and type Ia polysaccharides of group B. streptococci. Infect. Immun. 41:527–534.
10. Dillon, H. C., S. Khare, and B. M. Gray, 1987. Group B streptococcal carriage and disease: a six-year retrospective study. J. Pediatr. 110:31–36.
11. Dubois, M., K. A. Gilles, J. K. Hamilton, P. A. Rebars, and F. Smith. 1956. Colormetric method for the determination of sugars and related substances. Anal. Chem. 28:350–356.
12. Freimer, E. H. 1967. Type-specific polysaccharide antigens of group B streptococci, J. Exp. Med. 125:381–392.
13. Gelfaud, H. M., J. P. Fox, D. R. LeBlanc, and L. Elveback, 1960. Studies on the development of natural immunity to poliomyalitia in Louisiana. V. Passive transfer of polioantibody from mother to fetus, and natural decline and disappearance of antibody in the infant. J. Immunol. 85:46–55.
14. Goegel, W. F., and O. T. Avery, 1931. Chemo-Immunological studies on conjugates carbohydrate-proteins. IV. The synthesis of the p-amninobenzyle either of the soluble specific substance of type III pneumococcus and its coupling with protein. J. Exp. Med. 54:431–436.
15. Gray, B. M. 1979. ELISA methodology for polysaccharide antigens: protein coupling of polysaccharides for adsorption to plastic tubes. J. Immunol. Methods 28:187–192.
16. Hobbs, J. R., and J. A. Davis, 1967. Serum G-globulin levels and gestational age in premature babies. Lancet 493:757–759.
17. Insel, R. A., and P. W. Anderson, 1986. Oligosaccharide-protein conjugate vaccines induce and prime for oligoclonal IgG antibody responses to the *Haemophilus Influenzae* b capsular polysaccharide in human infants. J. Exp. Med. 163:262–269.
18. Jennings, H. J., and C. Lugowski, 1981. Immunochemistry of groups A, B, and C meningococcal polysaccharide tetanus toxoid conjugates. J. Immunol. 127:1011:1018.
19. Jennings, H. J., C. Lugowski, and F. E. Ashton, 1984, Conjugation of meningococcal lipopolysaccharide R-type oligosaccharides to tetanus toxoid as a route to a potential vaccine against group B *Neisseria meningitidis*. Infect. Immun. 43:407–412.
20. Jennings, H. J., K. H. Russell, E. Katzenellenbogen, and D. L. Kasper. 1983. Structural determination of the capsular polysaccharide antigen of type II group B Streptococcus. J. Biol. Chem. 258:1793–1798.
21. Kasper, D. L., C. J. Baker, B. Galdes, E. Katzenellenbogen, and H. J. Jennings. 1983. Immunochemical analysis and immunogenicity of the type II group B streptococcal capsular polysaccharide. J. Clin. Invest. 72:260–269.
22. Lagergard, T., J. Siloach, J. B. Robbins, and R. Schneerson. 1990. Synthesis and immunocological properties of conjugates composed of group B Streptococcus type III capsular polysaccharide covalently bout to tetanus toxoid. Infect. Immun. 58:687–694.
23. Lancefield, R. C. 1972. Cellular antigens of group B streptococci, p. 67–65. In L. W. Wannamaker and J. M. Matson (ed.), Streptococci and streptococcal diseases: recognition, understanding, and management. Academic Press, Inc. New York.
24. Lancefield, R. C., M. McCarty, and W. N. Everly. 1975. Multiple mouse-protective antibodies directed against group B streptococci. J. Exp. Med. 142:164–179.
25. Lowry, O. H., N. J. Rosebrough, A. L. Farr, and R. J. Randall. 1951. Protein measurement with the Folin phenol reagent. J. Biol. Chem. 193:265–275.
26. Michen, F., E. Katzenellenbogen, D. L. Kasper, and H. L. Jennings. 1987. Structure of the complex group-specific polysaccharide of group B Streptococcus. Biochemistry 26:476–486
27. Paoletti, L. C., D. L. Kasper, F. Michon, J. DiFabio, K. Holme, H. J. Jennings, and M. R. Wessels. 1990. An oligosaccharide-tetanus toxoid conjugate vaccine against type III group B Streptococcus. J. Biol. Chem. 265:18278–18283.
28. Paoletti, L. C., D. L. Kasper, F. Michon, H. J. Jennings, T. D. Tosteson, and M. R. Wessels. 1992. Effects of chain length on the immunogenicity in rabbits of group B Streptococcus type III oligosaccharide-tetanus toxoid conjugates. J. Clin. Invest. 89:203–209.
29. Schneerson, R. O. Barrera, A. Sutton, and J. B. Robbins. 1980. Preparation, characterization and immunogenicity of *Haemophilus influenzae* type b polysaccharide-protein conjugates. J. Exp. Med. 152:361–376.
30. Svenson, S. B. and A. A. Lindberg. 1979. Coupling of acid-labile Salmonella specific oligosaccharides to macromolecular carriers. J. Immunol. Methods 25:323–335.
31. Walsh, J. A., and S. Hutchins. 1989. Group B streptococcal disease: its importance in the developing world and prospect for prevention with vaccines. Pediatr. Infect. Dis. J. 8:271–276.
32. Warren, L. 1959. The thiobarbituric acid assay of sialic acids. J. Biol. Chem. 234:1971–1975.
33. Wessels, M. R., L. C. Psoletti, D. L. Kasper, J. L. DiFabio, F. Michon, K. Holme, and H. J. Jennings. 1990. Immunogenicity in animals of a polysaccharide-protein conjugate vaccine against type III group B Streptococcus, J. Clin. Invest. 86:1428–1433.
34. Zigterman, J. W. J. , J. E. G. van Dam, H. Snippe, F. T. M. Rottsveel, M. Janszs, J. M. N. Willers, J. P. Kamerling, and J. F. G. Vlegenthart. 1985. Immunogenic properties of octasaccharide-protein conjugates derived from Klebsiella serotype II capsular polysaccharide. Infect. Immun. 47:421–428.

While we have hereinbefore described a number of embodiments of this invention, it is apparent that the basic constructions can be altered to provide other embodiments which utilize the methods of this invention. therefore, it will be appreciated that the scope of this invention is defined by the claims appended hereto rather than by the specific embodiments which have been presented hereinbefore by way of example.

We claim:

1. An antigenic conjugate molecule comprising a capsular polysaccharide derived from Group B streptococcus type II and a protein component wherein two or more side chains terminating in sialic acid residues of the polysaccharide component are each linked through a secondary amine bond to protein and wherein the molecular weight of the polysaccharide is at least 5000 daltons.

2. The conjugate molecule according to claim 1 wherein between 5 and 50% of the terminal sialic acid residues of each polysaccharide are linked to protein.

3. The conjugate molecule according to claim 2 wherein between 5 and 25% of the terminal sialic acid residues of each polysaccharide are linked to protein.

4. The conjugate molecule according to claim 3 wherein between 5 and 10% of the terminal sialic acid residues of each polysaccharide are linked to protein.

5. The conjugate molecule according to claim 4 wherein 7% of the terminal sialic acid residues of each polysaccharide are linked to protein.

6. The conjugate molecule according to claim 1 wherein the antigenic conjugate molecule is capable of being filter sterilized through a 0.2 micron filter.

7. The conjugate molecule according to claim 1 wherein the polysaccharide component has a molecular weight of between about 5,000 and 1,000,000 daltons.

8. The conjugate molecule according to claim 7 wherein the polysaccharide component has a molecular weight of between about 50,000 and 500,000 daltons.

9. The conjugate molecule according to claim 8 wherein the polysaccharide component has a molecular weight of between about 100,000 and 300,000 daltons.

10. The conjugate molecule according to claim 9 wherein the polysaccharide component has a molecular weight of about 200,000 daltons.

11. The conjugate molecule according to claim 1 wherein the protein is selected from the group consisting of tetanus toxoid, diphtheria toxoid and CRM (cross reactive material) 197.

12. A method of preparing a conjugate molecule of a capsular polysaccharide of Group B streptococcus type II and a protein comprising (a) subjecting the Group B streptococcus type II capsular polysaccharide to periodate oxidation sufficient to introduce an aldehyde group into one or more terminal sialic acid residues linked to the backbone of the polysaccharide;

(b) coupling the oxidized Group B streptococcus type II capsular polysaccharide to a protein through reductive amination to generate a secondary amine bond between the capsular polysaccharide and the protein.

13. The method according to claim 12 wherein between about 5 and 50% of the sialic acid residues of each polysaccharide are oxidized to form aldehyde groups capable of coupling to protein.

14. The method according to claim 13 wherein between about 5 and 25% of the sialic acid residues of each polysaccharide are oxidized to form aldehyde groups capable of coupling to protein.

15. The method according to claim 14 wherein between about 5 and 10% of the sialic acid residues of each polysaccharide are oxidized to form aldehyde groups capable of coupling to protein.

16. The method according to claim 15 wherein about 75% of the sialic acid residues of each polysaccharide are oxidized to form aldehyde groups capable of coupling to protein.

17. The method according to claim 12 wherein between about 5 and 50% of the sialic acid residues of each polysaccharide are covalently linked to protein.

18. The method according to claim 17 wherein between about 5 and 25% of the sialic acid residues of each polysaccharide are covalently linked to protein.

19. The method according to claim 18 wherein between about 5 and 10% of the sialic acid residues of each polysaccharide are covalently linked to protein.

20. The method according to claim 18 wherein about 5% of the sialic acid residues of each polysaccharide are covalently linked to protein.

21. A conjugate molecule prepared according to the method of any one of claims 12 through 20.

22. A vaccine comprising the conjugate molecule according to any one of claims 1 through 11.

23. A multivalent vaccine comprising the conjugate molecule according to any one of claims 1 through 11 and at least one other immunogenic molecule capable of eliciting the production of antibodies to a pathogenic substance other than Group B streptococcus type II.

24. The multivalent vaccine according to claim 23 wherein the other immunogenic molecules are capable of eliciting the production of antibodies to pathogens selected from the group consisting of Group B streptococcus types Ia, Ib, III, IV and V, *Haemophilus influenzae* type b and *E. coli* type K1.

25. The multivalent vaccine according to claim 24 wherein the other immunogenic molecules are capable of eliciting the production of antibodies to pathogens selected from the group consisting of Group B streptococcus types Ia, Ib, III, *Haemophilus influenzae* type b and *E. coli* type K1.

26. The multivalent vaccine according to claim 25 wherein the other immunogenic molecules are capable of eliciting the production of antibodies to pathogens selected from the group consisting of Group B streptococcus types Ia, Ib, III and *E. coli* type K1.

27. The multivalent vaccine according to claim 26 wherein the other immunogenic molecules are capable of eliciting the production of antibodies to pathogens selected from the group consisting of Group B streptococcus types Ia, Ib, III.

28. A method of immunizing humans wherein a vaccine comprising the conjugate molecule according to any one of claims 1 through 11 is administered in an immunogenic amount to a human.

29. The method according to claim 28 wherein the vaccine is administered to a female between the ages of about 10 and 50 years of age.

30. A method of immunizing humans wherein a vaccine comprising the conjugate molecule according to any one of claims 1 through 11 is administered in an immunogenic amount to a person at risk for being infected by Group B streptococcus type II.

31. The method according to claim 30 wherein the vaccine is administered to a person whose immune system is suppressed.

32. The method according to claim 31 wherein immunosuppression is due to diseases selected from the group consisting of cancer or diabetes.

33. A method of immunizing dairy herds against bovine mastitis consisting of administering a vaccine comprising the conjugate molecule according to any one of claims 1 through 11 in an immunogenic amount to dairy cows.

* * * * *

UNITED STATES PATENT AND TRADEMARK OFFICE
CERTIFICATE OF CORRECTION

PATENT NO. : 5,843,461
DATED : December 1, 1998
INVENTOR(S) : Harold J. Jennings and Dennis L. Kasper It is certified that error appears in the above-indentified patent and that said Letters Patent is hereby corrected as shown below:

COLUMN 13, LINE 3, change "75" to --7--.

Signed and Sealed this

Twenty-sixth Day of October, 1999

Attest:

Q. TODD DICKINSON

*Attesting Officer*　　　*Acting Commissioner of Patents and Trademarks*